United States Patent
Thomé-Förster et al.

(10) Patent No.: US 7,110,181 B2
(45) Date of Patent: Sep. 19, 2006

(54) METHOD FOR GENERATING ELECTROMAGNETIC FIELD DISTRIBUTIONS

(75) Inventors: Heidi Thomé-Förster, Azmoos SG (CH); Claus Heine-Kempkens, Chur GR (CH)

(73) Assignee: Unaxis Balzers Ltd., Blazers (LI)

( * ) Notice: Subject to any disclaimer, the term of this patent is extended or adjusted under 35 U.S.C. 154(b) by 89 days.

(21) Appl. No.: 10/740,057

(22) Filed: Dec. 18, 2003

(65) Prior Publication Data

US 2004/0130787 A1    Jul. 8, 2004

Related U.S. Application Data

(60) Provisional application No. 60/434,987, filed on Dec. 19, 2002.

(51) Int. Cl.
*G02B 5/18* (2006.01)

(52) U.S. Cl. .................. 359/569; 359/566; 359/576; 359/587

(58) Field of Classification Search ............ 359/566, 359/568, 569, 572, 576, 584, 587
See application file for complete search history.

(56) References Cited

U.S. PATENT DOCUMENTS

| 5,210,404 | A | | 5/1993 | Stewart |
| 5,907,436 | A | * | 5/1999 | Perry et al. .............. 359/576 |
| 6,483,959 | B1 | | 11/2002 | Goddard |
| 2002/0021445 | A1 | | 2/2002 | Bozhevolnyi |

FOREIGN PATENT DOCUMENTS

| WO | 98 08219 A | 2/1998 |
| WO | 01 79821 A | 10/2001 |

* cited by examiner

*Primary Examiner*—Leonidas Boutsikaris
(74) *Attorney, Agent, or Firm*—Pearne & Gordon LLP

(57) ABSTRACT

This invention relates to a platform (11) and a method for generating electromagnetic field distributions. The invention relates in particular to optical sensors for measuring biological or chemical substances. The platform (11) according to the invention comprises a substrate (13), a structured layer (19) and, positioned between the substrate (13) and the structured layer (19), a multilayer assembly (17), said components being so matched relative to one another that upon appropriate impingement by electromagnetic radiation an electromagnetic field distribution is generated that is at a maximum within the structured layer (19).

13 Claims, 4 Drawing Sheets

METHOD FOR GENERATING ELECTROMAGNETIC FIELD DISTRIBUTIONS

BACKGROUND OF THE INVENTION

This invention relates to a system and a method for generating electromagnetic fields in areas accessible to substances to be irradiated. This invention relates in particular to optical sensors for measuring biological or chemical substances.

Electromagnetic fields are utilized in numerous applications for detecting minute concentrations of substances most typically in liquid samples. There are two basic categories of optical sensors designed to detect substance accumulations on the detector surface: Those used for labeled substances (label methodology) and those that function without such labeling (non-label methodology).

Label methodology encompasses, inter alia, a method whereby the substances to be detected are labeled with a fluorescent dye. Examples of commercially available fluorescent dyes include CY5 for an excitation wavelength of 532 nm, and CY3 for an excitation wavelength of around 635 nm.

While such labeling may be selective, it usually also covers other substances that are present in a sample to be measured. In cases of nonselective labeling, selectivity can be achieved for instance by applying on the surface of the sensor a treatment that allows only the labeled substance that is to be measured to selectively adhere to that surface. When, after full adhesion, the surface is flushed, the intensity of the resultant fluorescence signal provides a quantitative indication of the concentration of the substance to be measured in the sample concerned. Such quantitative information can also be obtained without flushing whenever it is possible to cause a fluorescence-stimulating electromagnetic field to attach itself in concentrated and essentially dedicated fashion to the substances that are to be detected on the sensor surface.

As long as not all of the labeled substances adhering to the surface fluoresce, this general rule applies: the higher the electromagnetic field intensity generated on the surface relative to the impinging light intensity, the better the signal-to-noise (S/N) ratio of the measurement. This has a direct effect on the measuring sensitivity of the sensor. Accordingly, one will try to produce on the surface area concerned as strong an electromagnetic field as possible in relation to the volume to be measured.

Apart from the label-based methods described, i.e. marker-based measuring techniques, non-label methods are widely used as well. In that case, it is for instance a change of the angle of refraction caused by the accumulation of the substance to be measured on the sensor surface that is a factor directly influencing the field distribution in the sensor. That factor has an effect on such optical measuring parameters as the diffraction coefficient or perhaps the waves that pass through a fiber-optic cable, triggering mensurable changes. Here as well it is important that at least segments of the substances being measured have areas accessible to electromagnetic fields.

One possibility to build up that kind of field distribution accessible to the substance being measured is to utilize cross-attenuated electromagnetic waves. In the simplest case a one-time total internal reflection (TIR) is used. To that end, excitation light emanating from the substrate impinges on the sensor surface at an angle that is greater than the critical total reflection angle. This generates on the surface a cross-attenuated field which, declining exponentially, projects from the substrate into the medium to be measured. Technical literature also refers to these fields as evanescent fields, since no light propagates into the medium to be measured but, instead, the field only "projects" into the medium and is thus restricted to the immediate contact surface within the corresponding boundaries.

The so-called depth of penetration, meaning the distance from the contact surface at which the field intensity has dropped to 1/e (where e is the Eulerian coefficient), depends among other factors on the actual angle of incidence and is typically measured in units of the vacuum wavelength of the excitation energy while being of the same order of magnitude.

One way to elevate this type of evanescent field relative to simple total reflection is to cause the excitation light energy to reflect off the contact surface multiple times. For example, if an optical layer of a specific thickness and with a high refractive index relative to the substrate is applied on the latter, it is possible, under certain conditions, for total reflection to take place on both contact surfaces of the layer and for the light propagation to be guided within the layer in a so-called waveguide mode. In a suitably selected waveguide configuration, this leads to an elevated evanescent field on the surface of the waveguide.

It is important in this context that the wave-conducting layer, meaning the layer in which the light wave is guided, have a refractive index that is greater than the refractive indices of the substrate and of the medium next to the waveguide layer. Otherwise there cannot be multiple total reflections nor, consequently, any wave propagation (refer for instance to WO 86/071149). For a given substrate the choice of materials for the wave-conducting layer is therefore limited to high-refraction materials.

Another problem is posed by the fact that the mode propagation and thus the intensity of the field that is available for excitation depends in highly sensitive fashion on the waveguide configuration and possibly existing imperfections. Even minute impurities cause light scattering and a diminution of the intensity of the light passing through the waveguide. That effect is integrally propagated over the entire distance of the light path through the waveguide and even in the case of minute impurities and/or defects it can produce incorrect measurements.

Another difficulty is encountered when coupling the light into the waveguide, which can be accomplished through end-face interfacing, prismatic coupling or via a coupler grating. In all of these it is difficult to ensure constancy in terms of coupling efficiency which, however, should preferably be obtainable for quantitative measurements.

As another problem, the density of the various measuring ranges is limited due to the expansion of the waveguide.

Another way to arrive at an elevated evanescent field is to stimulate so-called surface plasmons. These excitation conditions, generated in metallic layers, propagate in the plane of the layer until they fall apart for instance by absorption in the metal or by scattering. Here again, controlling the evanescent field intensity produced by surface plasmons is quite difficult. And again, there is a limit to the density of the measuring ranges since surface plasmons usually travel over finite distances only before they decay. Moreover, in many cases, metals have stability problems and most of all they tend to age, potentially leading to unreliable measurements.

More recent approaches utilize the well-known effect of the resonant grating with anomalous transmission breaks, for instance as described by Novartis in WO2001/002839 (hereinafter referred to as the Novartis application). As in the case of the waveguide, the substrate is coated with a layer whose refractive index is higher than the refractive index of the substrate, since otherwise there would be no resonance effect. In addition, the surface area of the measuring field is defined by a periodic pattern of channels.

The dimensions of the structures and layers are so chosen that the impingement of coherent light at a particular angle causes a resonance effect whereby transmission is reduced in anomalous fashion, building up the desired evanescent field. The advantage of that approach is that it is not necessary for the light to travel waveguide-style over a long distance, making the system substantially less sensitive to imperfections and centers of scattering. Moreover, compared to waveguide coupling provisions the system can be smaller in size, allowing for a considerably larger number of measuring ranges since for all practical purposes the light does not propagate laterally. This advantage of a potentially greater density of measuring ranges has been stressed most of all in WO2000/75644 by Zeptosens (hereinafter referred to as the Zeptosens application). The Zeptosens application as well provides for continuous modulations in the measuring range, although it is still based on a laminar optical waveguide.

Both the waveguide approach for generating a high field intensity in the surface area and the resonant-grating approach employing anomalous transmission suffer from a drawback in that the field intensity obtained on the surface is a mere fraction of the field intensity present in the highly refractive layer and perhaps in the wave-conducting layer. In these systems, only the cross-attenuated evanescent spurs of the field are accessible.

Another disadvantage lies in the fact that in the cases concerned a highly refractive layer must serve as the terminal surface relative to the surrounding medium. The most progress here has been made in biochemical applications on $SiO_2$ surfaces. With glass substrates, other materials must be used for producing a layer which compared to the substrate has a high refractive index. Examples of the materials employed include $TiO_2$ or $Ta_2O_5$. Compared to $SiO_2$, however, these materials have been less widely adopted for biochemical applications. It is possible to coat the high-refraction layer with a thin film of $SiO_2$, which in fact must be very thin since the decline of the evanescent field is exponential in this film as well.

BRIEF SUMMARY OF THE INVENTION

It is the objective of this invention to overcome the shortcomings described above. In particular, the invention is aimed at introducing a system by means of which an elevated field intensity can be generated without the maximum field intensity that is accessible to the measuring substance being limited to the evanescent components of the field intensities that build up in the system. Another aspect of the invention consists in the generation of high, not only evanescent field intensities in surface layers whose refractive index is not higher, or only insignificantly higher (<1%), than the refractive index of the substrate. Another objective of this invention is to introduce a method by means of which such field intensities can be obtained.

According to the invention, this objective is achieved by means of a platform for generating an electromagnetic field distribution as specified in claim 1.

A platform of that type includes
a substrate
a structured layer provided on the substrate, with the thickness of the structured layer being determined by the maximum depth of the structured surface profile,
means for coupling incident electromagnetic radiation into the structured layer for generating an electromagnetic field distribution within the structured layer,
a multilayer assembly provided between the substrate and the structured layer, preferably for the at least partial inhibition of the coupling of the electromagnetic fields, generated in the structured layer, to higher than zero-order diffractions propagating into the substrate, with the structured layer, the coupling means and the multilayer assembly being so matched relative to one another as to cause an appropriate impingement of electromagnetic radiation on the platform to maximize the resulting electromagnetic field intensity within the structured layer.

One form of implementation of the platform is further characterized in that the refractive index or, as appropriate, the effective refractive index of the structured layer is higher by less than 1%, but preferably smaller, than the refractive index of the substrate.

Another form of implementation of the platform is further characterized in that the surface profile of the structured layer encompasses essentially periodic conformations that constitute components of the coupling means.

Again another form of implementation of the platform is additionally characterized in that the multilayer assembly encompasses metallic layers preferably consisting of Al, Ag, Au, combinations thereof, or other suitable materials.

Another form of implementation of the platform is characterized in that the layer assembly encompasses dielectric layers and preferably no metallic layers, with the layer system preferably consisting of alternating high and low refraction layers.

Other design versions of the platform are characterized in that the type of structural surface profile, the coupling means as well as the number, material and thickness distribution of the layers in the multilayer assembly are selected in such fashion that, upon impingement of electromagnetic radiation on the platform, the resulting field-intensity distribution in the areas that are devoid of any layer material includes at least one maximum.

With a platform according to the invention it is possible to produce a field-distribution configuration that additionally incorporates a source for generating electromagnetic radiation and an electromagnetic field whose intensity is at a maximum in the region of the structured layer.

In a special form of implementation of the said field-distribution platform, the electromagnetic field distribution in the regions of the structured layer that are devoid of any layer material displays at least one maximum.

The above-mentioned platforms and field distribution configurations may be part of a sensor that serves to measure specific substances in a biological and/or chemical and/or biochemical sample.

The objective of introducing a method by which an elevated and not merely evanescent field distribution can be generated is achieved with the following steps:
Selection of a substrate
Selection of the material and surface profile of a structured layer
Selection of the materials for a multilayer assembly
Definition of the parameters of the impinging electromagnetic radiation
Simulation and optimization of the electromagnetic field distribution within a platform that encompasses the substrate, the multilayer assembly and the structured layer upon impingement by electromagnetic radiation of the predefined parameters, with the multilayer assembly positioned between the substrate and the structured layer and the optimization objective being a field distribution that is at a maximum within the structured layer;

Build-up of a platform that at least approximates the optimization result;

Exposure of the platform to electromagnetic radiation along the predefined parameters.

Another form of implementation of the method is aimed, as its optimization objective, at an electromagnetic field distribution that exhibits at least one maximum in the regions of the structured layer that are devoid of any layer material.

The invention thus achieves its objective by the skilful combination of the properties of the dielectric multilayer assembly and of optical gratings. This circumvents the principle of wave conduction in highly refractive layers as well as the principle of anomalous reduction of the transmission of resonant gratings. Instead, the substrate is coated with a dielectric alternating-layer assembly on which a diffraction grating is provided.

Structural configurations of this nature have been described in literature on applications where for instance the peak response of the spectral orders is to be set at particular values. For example, in U.S. Pat. No. 5,907,436 (hereinafter referred to as Perry '436), Perry et al describe this kind of structure whose configuration is so selected that the proportions of incident light, reflection and transmission of the zero and higher diffraction orders are predetermined by the number of layers, the thickness of at least one of the layers and the depth and shape of the grating structure.

According to the invention, this type of system is specifically or additionally optimized insofar as the optimized system exhibits a high or even the highest field intensity in the area of the surface structures and especially in the area of the troughs or valleys of the grating. In this fashion, systems are obtained in which, upon impingement of the electromagnetic radiation selected for optimized performance, a field distribution is generated that exhibits maxima in the grating valleys that are accessible for the measurement.

For optimization both local and global optimizing methods are suitable. Those skilled in the art of optical coatings, for instance for optimizing optical alternating layer assemblies, will be familiar with either method. But employing such optimizing methods in connection with the optimization objective here discussed is new and inventive. Of course, the expert will know how to go about it once the new aspect has been disclosed to him, optimizing electromagnetic field intensity in certain regions of the structure, correspondingly employing the system parameters as optimization parameters, with particular emphasis on layer thickness and grating depth. This fully discloses the technical concept applied.

If for a better understanding it is still necessary to provide a more detailed explanation, the multilayer assembly may be viewed as a means for decoupling the structured layer from the substrate with regard to higher spectral orders. The coupling and decoupling of electromagnetic radiation into/from the structured layer is then essentially limited to the zero diffraction order in the transmission or reflection mode. This can lead to the generation of strong electromagnetic fields within the structured layer, especially when the diffraction structures offer weak diffractive efficacy.

Since these detailed explanations, especially in a case such as the one here discussed, can correctly describe the underlying physics to a limited extent only, it is stressed once again that those skilled in the art involving optical multilayer assemblies and diffraction gratings and their optimization will have to extend their optimizing strategy to the optimization of electromagnetic field distributions in order to arrive at a system according to this invention, with the solution, outlined above, for achieving the technical objective here discussed.

This field distribution can be obtained especially with a system whose homogeneous layer on which the grating is positioned, and/or the grating structure may consist of a low-refraction material and in particular of a material whose refractive index is lower than or equal to the refractive index of the substrate. That also makes it evident that the effect here discussed is not based on, nor can it be derived from, that of the waveguide which is linked to a high refractive index and on the electromagnetic fields associated therewith, nor on/from the effect of the resonant grating linked to a high refractive index in connection with reflection or transmission anomalies. In contrast thereto it is entirely possible to produce systems according to this invention which, contrary to prior art, essentially inhibit reflection, a fact that can be quite advantageous as will be explained further below.

DETAILED DESCRIPTION OF THE INVENTION

The following examples describe this invention in detail with reference to the diagrams.

Figure 1:
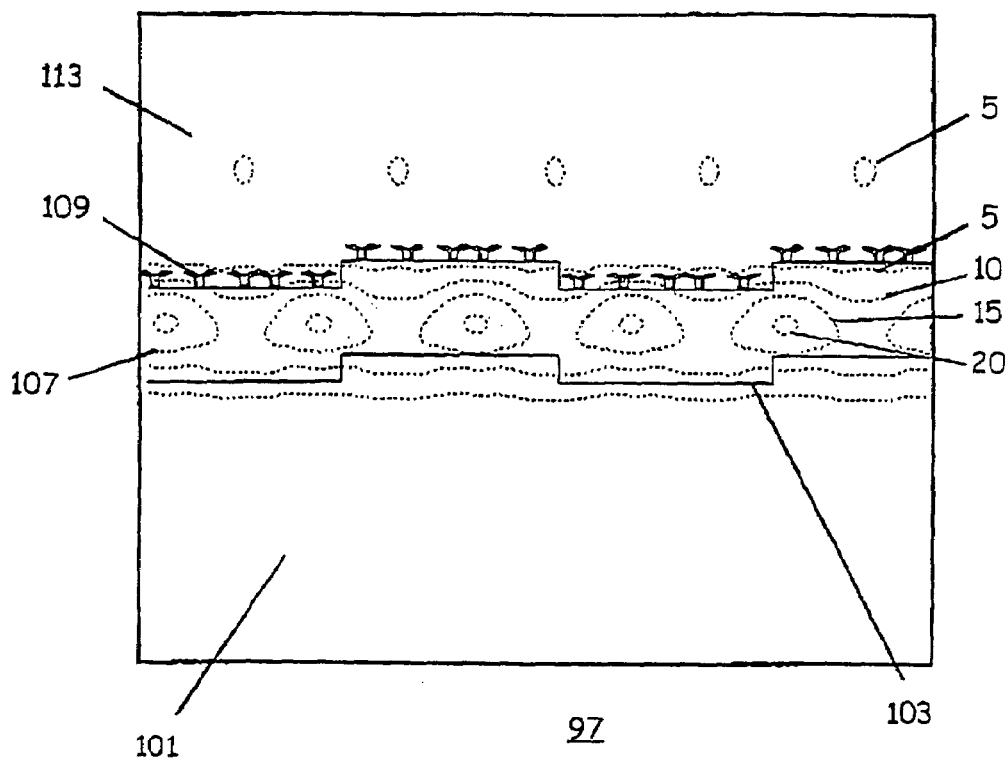
FIG. 1 is a schematic illustration of a prior-art structure as described in the Novartis application. The graph also shows the field distribution generated in this structure by impinging light.

For a better understanding of the underlying concept of this invention it will be helpful to first analyze in depth a typical prior-art example as disclosed in the Novartis application. That type of system 97 is schematically illustrated in FIG. 1. It comprises a structured substrate 101 with a refractive index of n=1.52 and incorporating a periodic grating with a grating periodicity of 360 nm and a grating depth of 38 nm. The structured substrate 101 is coated with a dielectric layer having a refractive index of n=2.2 and a thickness of 130 nm. The refractive index of that layer is thus significantly higher than that of the substrate. In this case the grating profile of the substrate is carried over to the surface that constitutes the interface with the surrounding medium, hereinafter referred to as the superstrate 113. The drawing also shows biological binder molecules 109 as used for instance in an antibody/antigen reaction.

In the example, the system is exposed to light at a wavelength of 633 nm impinging at an angle of incidence of $\delta_1$=2.9° with TE polarization. This angle corresponds to the resonance angle of the system with anomalously reduced transmission. The impingement takes place from the side of the superstrate. Together with the surface normal the light beam impinging on the high-refraction layer defines the plane of incidence. The impingement takes place in such fashion that the grating ridges extend vertically through this plane of incidence, meaning that in the example at hand it is not conical impingement. The TE polarization is characterized by the fact that the electric field vector oscillates in the plane perpendicular to the plane of incidence.

The additional dotted lines in FIG. 1 represent lines of equal square amplitudes of the field distribution. The reference numbers 5, 10, 15 and 20 indicate the corresponding values of the square amplitudes. All data in this document that refer to square amplitude values are data that relate to the square amplitude of a plane wave. In other words, the impinging light has a square amplitude of 1. A reference number is shown for only one of the maxima. One will notice that the maxima of the square amplitude are embedded in the high-refraction layer in totally inaccessible fashion for the substances to be measured and that the biological coupling elements come in contact merely with the evanescent spurs of the field.

Figure 2:
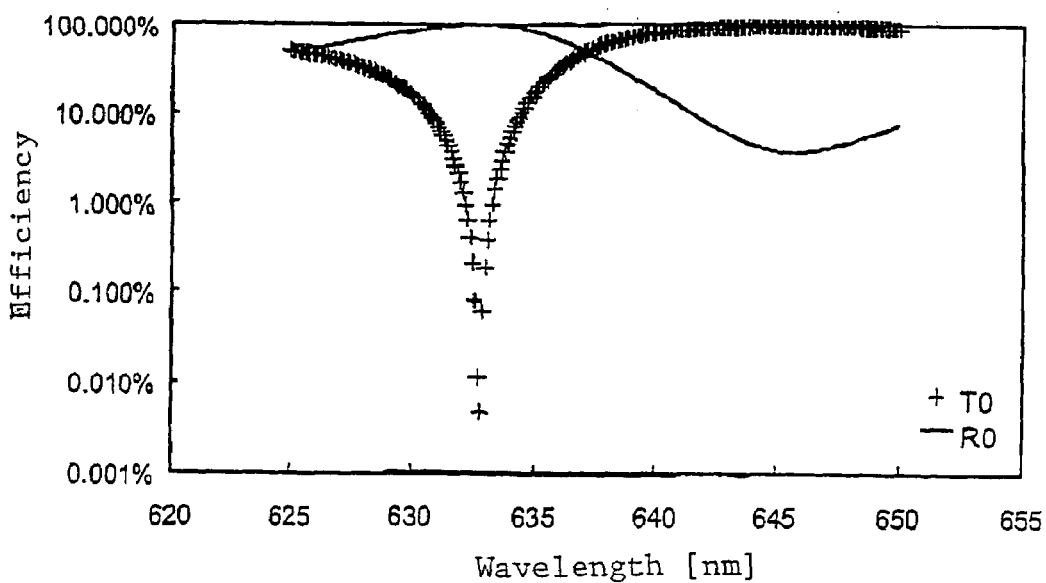
FIG. 2 shows the interdependence, per FIG. 1, of reflection and transmission as a function of wavelength. The anomalous reduction of the transmission to less than 1% is clearly visible.

Looking at the diffraction efficiencies as a function of wavelength, shown in FIG. 2, it is evident that in this case all of the impinging energy is concentrated in the zero diffraction order, which is the basis of the resonance effect employed in prior art. Moreover, at a wavelength of 633 nm a near 100% reflection is obtained whereas, correspondingly, the transmission recedes to nearly 0%, i.e. the effect of anomalous transmission reduction can be seen at 633 nm. To underscore the resonance effect, FIG. 2 is plotted along a logarithmic scale.

Figure 3:
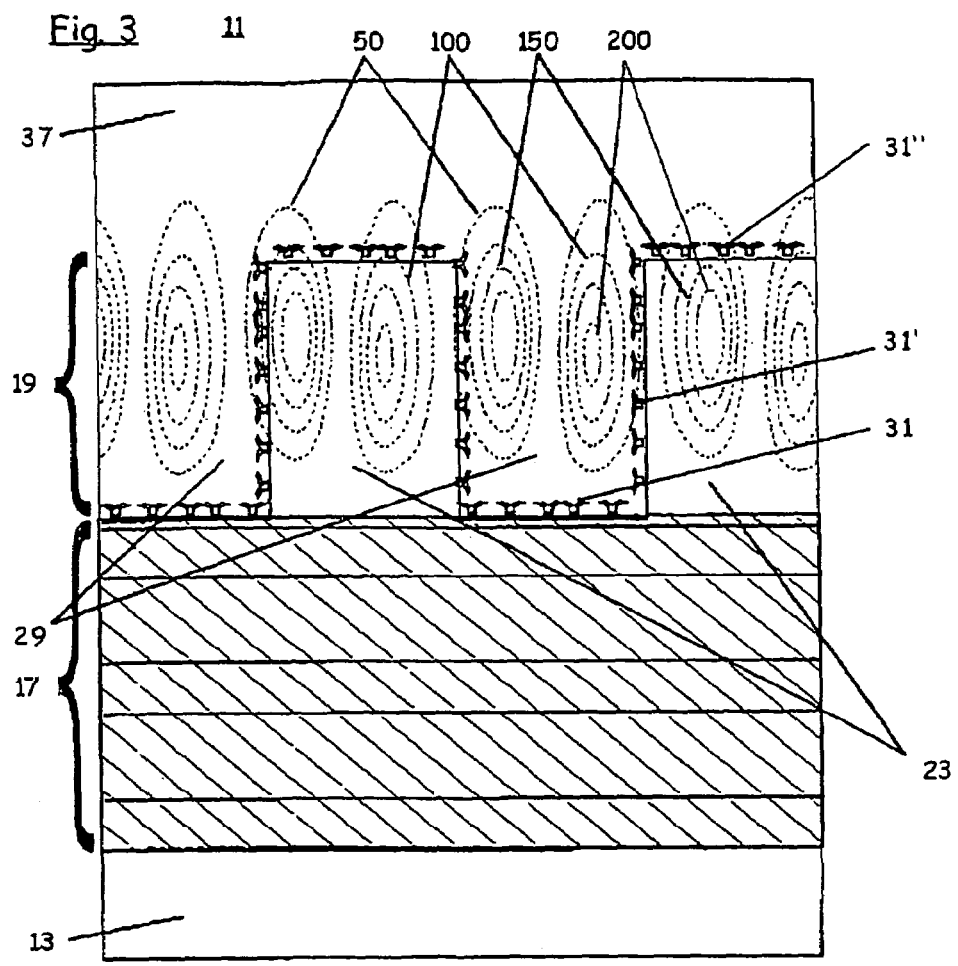
FIG. 3 is a schematic illustration of one design implementation of a structure according to this invention. This figure also shows the field distribution that builds up as the light impinges.

The first example of this invention, schematically illustrated in FIG. 3, discloses a system 11 per the invention that is implemented on a substrate 13 having a refractive index of about n=1.52, which would normally correspond to the refractive index for instance of BK7 or similar glass. Applied on this substrate is a dielectric layer assembly 17 composed of 6 layers. The first layer has a refractive index of about n=2.35, which can be obtained using for instance TiO$_2$. The second layer has a refractive index of about n=1.48 that may be obtained for instance with SiO$_2$. The layer assembly ends with a topmost layer of SiO$_2$, on which a periodic grating structure is applied. The grating periodicity is at 550 nm. The material of the grating ridges has a refractive index of about n=1.48 that could be obtained by surface-structuring a SiO$_2$ layer. The refractive index of the grating valleys is about n=1, i.e. that of air or a vacuum or the like. The example described uses a rectangular grating with a periodicity of 550 nm and with equidimensioned ridges and valleys, the space factor thus being f=0.5. The medium next to the grating, again referred to as the superstrate 37, has the same refractive index of n=1, meaning that the grating constitutes the terminating interface between the system and the surrounding medium. Accordingly, the grating valleys are freely accessible for the application, accumulation and measuring of substances.

In the example shown, light of a wavelength of 633 nm impinges on the system, from the side of the superstrate, at an angle of incidence of $\delta$=2° with TE polarization. Together with the surface normal the light beam impinging on the last layer defines the plane of incidence. The impingement takes place in such fashion that the grating ridges extend vertically through this plane of incidence, meaning that in the example at hand it is not conical impingement. The TE polarization is characterized by the fact that the electric field vector oscillates in the plane perpendicular to the plane of incidence. Accordingly, with the exception of the angle of incidence, the light-wave impingement conditions are identical to those of the prior-art example described.

For fully defining the system the only additional data needed relate to the thickness values of the individual layers and to the depth of the structured grating surface. These values were determined employing statistical optimization. In terms of the optimizing objective there are different possibilities. In the example at hand the optimization objective was to define the maximum field intensity at one point in the region within the grating valleys. Optimization can be obtained both by local and global methods with which those skilled in the art of optimizing for instance optical alternating layer assemblies using thin-film technology are quite familiar. However, employing such optimization methods in connection with the application here discussed is both novel and inventive. Of course, the expert will know how to go about it once the new aspect has been disclosed to him, optimizing the field intensity and correspondingly employing the system parameters as optimization parameters, with particular emphasis on layer thickness and grating depth. This fully discloses the technical concept applied.

The following table shows the results of such optimization:

TABLE 1

| | Refractive Index | Layer Thickness or Depth of Grating [nm] | Example |
|---|---|---|---|
| Superstrate | 1 | | Air |
| Grating | 1.48 and 1 | 387 | SiO$_2$ and Air |
| Layer 6 | 1.48 | 10.3 | SiO$_2$ |
| Layer 5 | 2.35 | 74.6 | TiO$_2$ |
| Layer 4 | 1.48 | 129.6 | SiO$_2$ |
| Layer 3 | 2.35 | 76.3 | TiO$_2$ |
| Layer 2 | 1.48 | 127.9 | SiO$_2$ |
| Layer 1 | 2.35 | 75.7 | TiO$_2$ |
| Substrate | 1.52 | — | BK7 |

FIG. 3 is a schematic illustration of the system 11 described in the example. Applied on the substrate is the layer assembly 17 composed of 6 layers. A grating structure 19, encompassing grating ridges 23 and grating valleys 29, is provided on the layer assembly 17. The grating periodicity is 550 nm. FIG. 3 also shows biological binder molecules 31, 31', 31" on the surface as used for instance in an antibody-antigen reaction. There may be binder molecules 31 that sit on the bottom of the valleys, perhaps binder molecules 31' that are attached to the lateral walls, and perhaps binder molecules 31" that sit on the grating ridges. Of course, other grating profiles are possible as well, for instance sinusoidal or projecting profiles, permitting the attachment of coupling elements in all locations. The additional dotted lines in FIG. 3 represent lines of equal square amplitudes of the field distribution. The reference numbers 50, 100, 150 and 200 indicate the corresponding values of the square amplitudes. It should be noted that in the valleys 29 of the grating structure a maximum square amplitude of over 200 is obtained. These maxima are substantially greater than those attainable in prior art and in contrast to the latter they are fully accessible to the substances to be measured.

As can be seen in FIG. 3, the entire maximum field distribution is limited to the area of the grating, again making it a novel system compared to prior art since each of the materials constituting the grating has a refractive index that does not exceed the refractive index of the substrate and may even be substantially lower.

Figure 4:
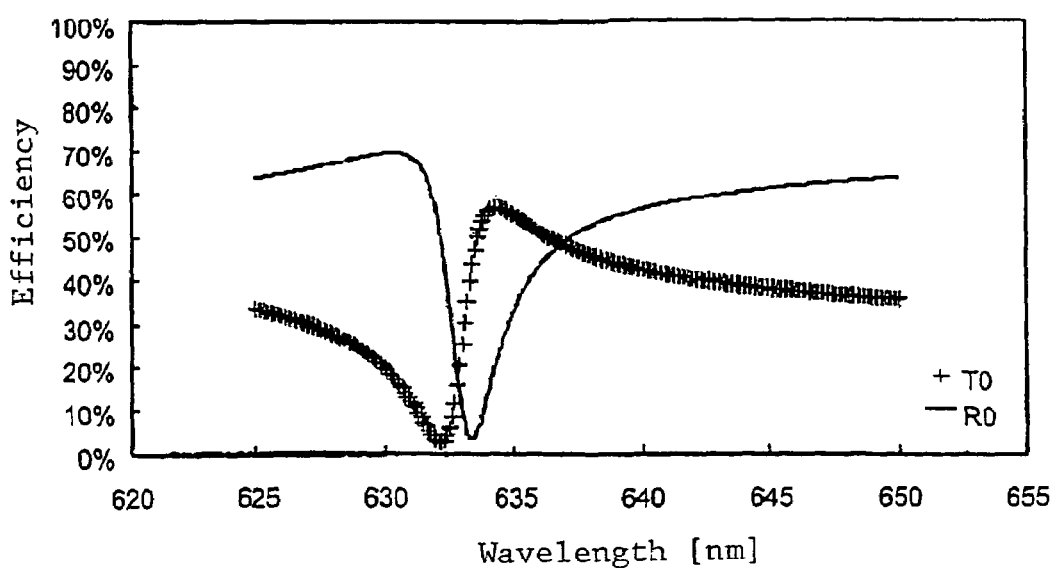
FIG. 4 shows the interdependence in the system per FIG. 3 of reflection and transmission as a function of wavelength. The spectra exhibit neither anomalous reflection nor anomalous transmission.

As described above, the resonant grating effect known from prior art that results in an anomalous transmission reduction is accompanied by a near 100% reflection. FIG. 4 illustrates the dependence of the diffraction efficiencies as a function of the wavelength of the light in the case of the above-described first example of this invention. It can be clearly seen that over the entire wavelength range in question the reflection does not exceed 70% while the transmission in the zero order does not drop below 2%. At the wavelength of 633 nm investigated in this example, the reflection is 14% while the zero-order transmission is about 25%.

In the second example described below, the reflection of the system has even been brought to less than 10%. The system 211 again encompasses a substrate 223, a layer assembly 227, a grating section 229 with a periodicity of 550 nm, biological coupling elements 233, 233', 233", and a superstrate 239. The type of impinging light is the same as in the first example. The required optimization objective was to maintain low reflection while still obtaining a high field intensity in the grating valleys. The system was composed in a fashion analogous to that in the first example, except that 16 layers were provided for optimization and $Ta_2O_5$ layers were used in lieu of $TiO_2$ layers. Thickness optimization of the layers resulted in the following system:

|  | Refractive Index | Layer Thickness or Depth of Grating [nm] | Example |
|---|---|---|---|
| Superstrate | 1 |  | Air |
| Grating | 1.48 and 1 | 300 | $SiO_2$ and Air |
| Layer 16 | 1.48 | 68.3 | $SiO_2$ |
| Layer 15 | 2.1 | 92.6 | $Ta_2O_5$ |
| Layer 14 | 1.48 | 181.9 | $SiO_2$ |
| Layer 13 | 2.1 | 93.3 | $Ta_2O_5$ |
| Layer 12 | 1.48 | 204.9 | $SiO_2$ |
| Layer 11 | 2.1 | 77.7 | $Ta_2O_5$ |
| Layer 10 | 1.48 | 286.8 | $SiO_2$ |
| Layer 9 | 2.1 | 73.7 | $Ta_2O_5$ |
| Layer 8 | 1.48 | 126.1 | $SiO_2$ |
| Layer 7 | 2.1 | 77.7 | $Ta_2O_5$ |
| Layer 6 | 1.48 | 124.0 | $SiO_2$ |
| Layer 5 | 2.1 | 76.7 | $Ta_2O_5$ |
| Layer 4 | 1.48 | 292.7 | $SiO_2$ |
| Layer 3 | 2.1 | 76.3 | $Ta_2O_5$ |
| Layer 2 | 1.48 | 119.0 | $SiO_2$ |
| Layer 1 | 2.1 | 79.6 | $Ta_2O_5$ |
| Substrate | 1.52 | — | BK7 |

Figure 5:
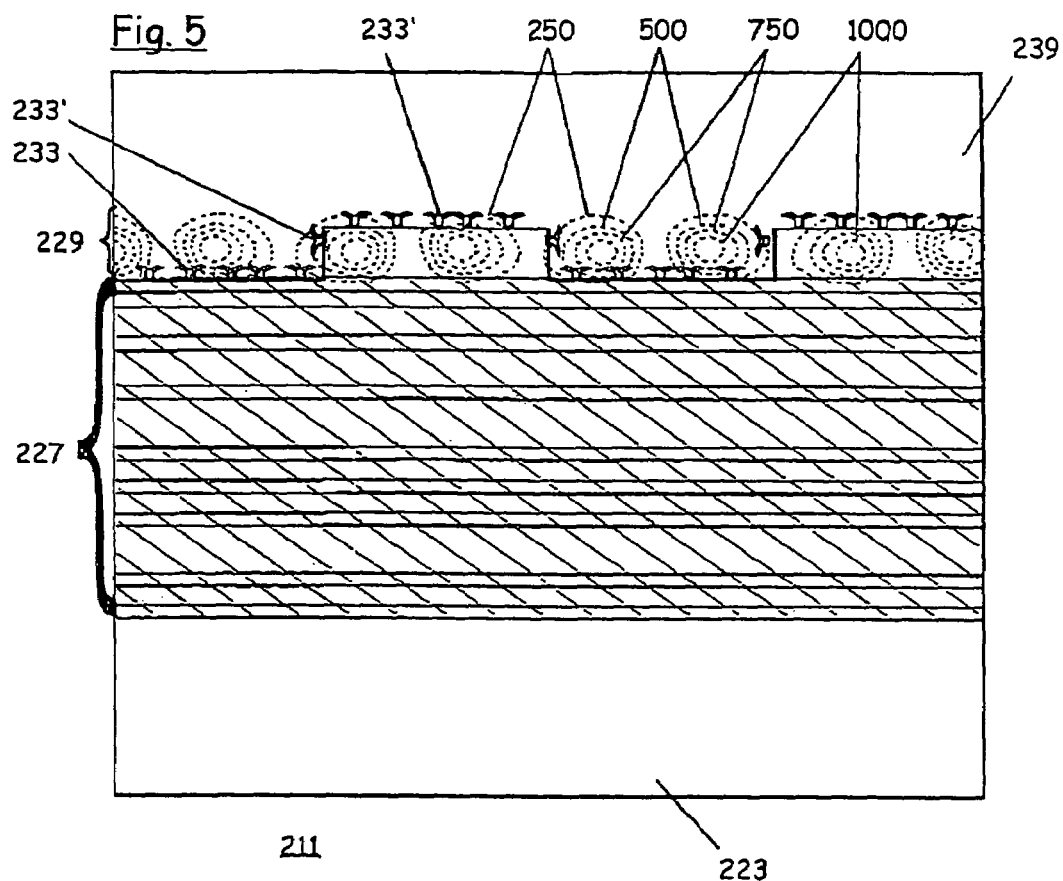
FIG. 5 is a schematic illustration of another advantageous form of implementation of a structure according to this invention.

FIG. 5 is a schematic illustration, comparable to that in FIGS. 1 and 3, of this system and of the associated field distribution. For illustrative purposes, however, FIG. 5 shows the extension in the direction of the layer planes at a double-enlarged scale compared to the extension in the direction of the respective layer thickness. The additional dotted lines in FIG. 5 represent lines of equal square amplitudes of the field distribution. The reference numbers 250, 500, 750 and 1000 indicate the corresponding values of the square amplitudes. As can be seen, a high field intensity has been generated in the grating valleys.

Figure 6:
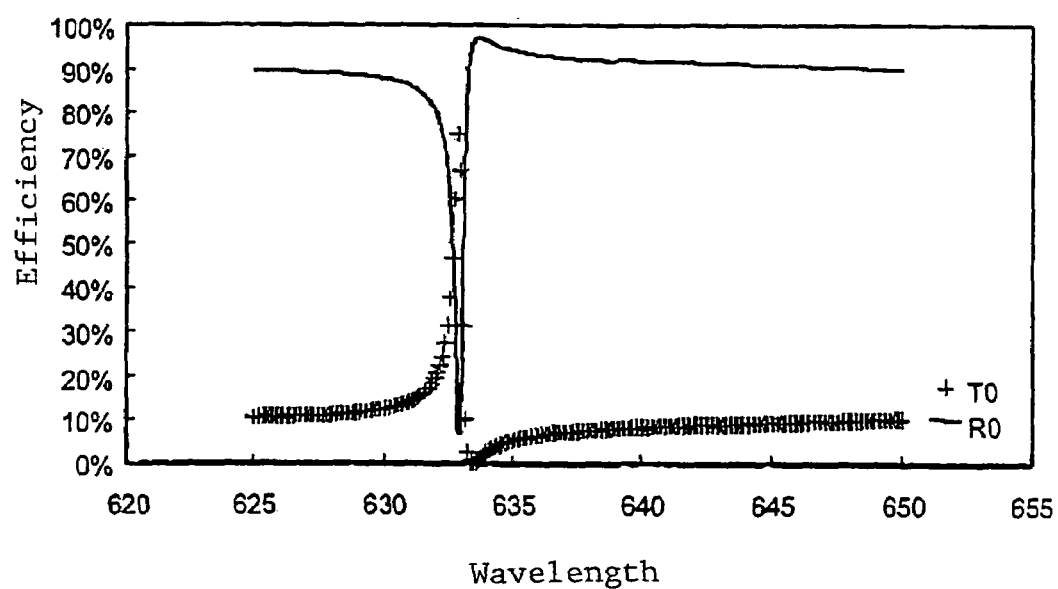
FIG. 6 shows the interdependence in the system per FIG. 5 of reflection and transmission as a function of wavelength. It can be clearly seen that in this case the reflection drops to below 1%.

The related FIG. 6 shows the reflection and transmission as a function of the wavelength. As is evident, the reflection does not come close to 100% at any wavelength within the range of interest. Quite probably there is a resonance effect which, however, is obviously different from that described in prior art (Novartis application).

Figure 7:
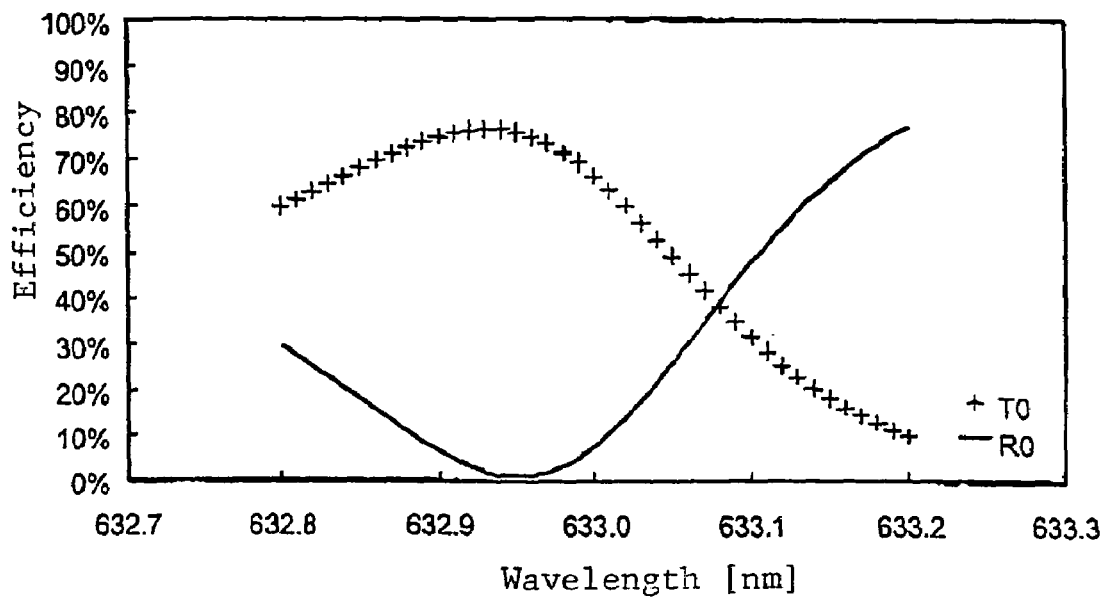
FIG. 7 is a graph corresponding to FIG. 6 for the range from 632.8 nm to 633.2 nm. It is evident that at a wavelength of 632.95 any reflection can be suppressed altogether.

FIG. 7 corresponds to FIG. 6 except that it represents the wavelength range from 632.8 nm to 633.2 nm. It shows that at a wavelength of 632.95 nm the reflection can actually be totally suppressed. In Perry '436 the grating periodicity was not an optimization parameter since the factors of significance also include diffraction efficiencies and their direction of propagation even in higher spectral orders. These directions are determined by the grating periodicity. Given that for the purpose of this invention they initially play a sub-ordinated role, the grating periodicity is a free parameter that can be suitably integrated in the optimization process. That in turn makes it possible to adapt the grating, for instance by scaling, in such fashion that minimum reflection occurs at the desired wavelength (in this example at 633 nm). This is particularly advantageous when one must make sure that none of the excitation light is reflected to the fluorescence-light detector.

Figure 8:
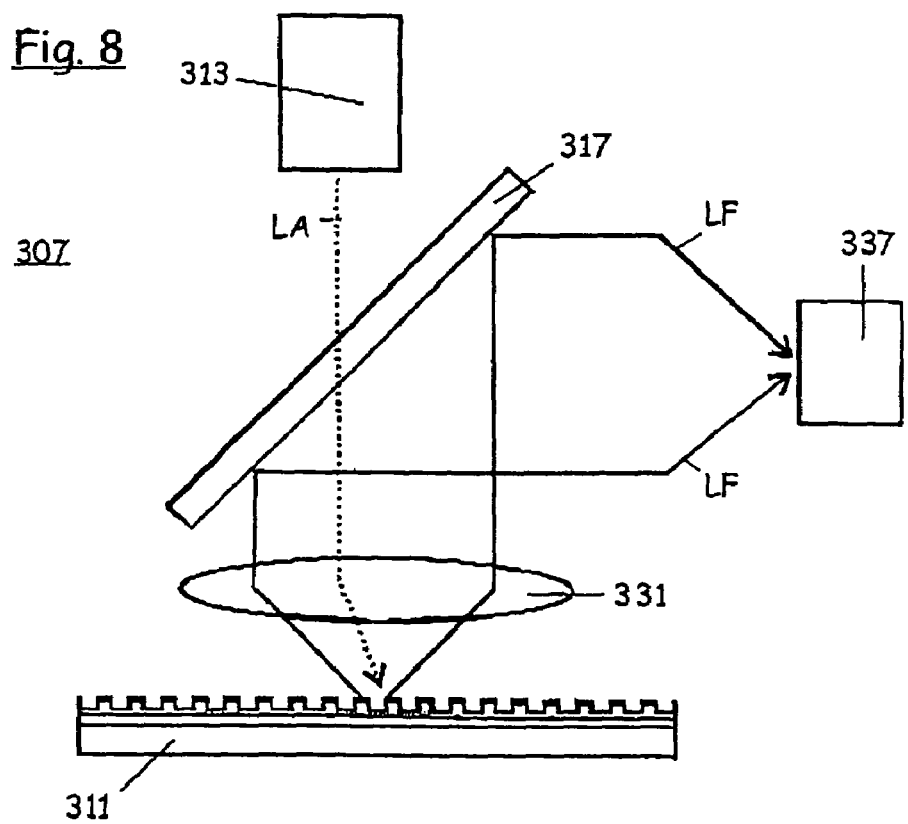
FIG. 8 depicts a measuring system according to this invention, for the selective detection of substances to be measured.

FIG. 8 is a schematic example of a possible design configuration of a measuring system 307. It is the specific fluorescence-labeled substances coupled on the measuring chip 311 that are to be measured. An essentially parallel excitation light beam LA impinges on the measuring chip 311 at a precisely defined angle. This can be accomplished for instance by directing a collimated light beam through a lens 331. In the example shown, the excitation beam emanates from a light source 313, is transmitted by a selective mirror 317 and through the lens 331 and strikes the surface of the measuring chip 311. At this point, a strong electromagnetic field is generated in the area of the grating, stimulating the specific surface-bound substance to be measured to fluoresce. Thereupon, fluorescent light LF travels to the lens 331. Since that surface is located in the focal plane of the lens 313, the fluorescent light LF will travel as an essentially parallel light beam to the selective mirror 317 from where it is reflected toward a detector 337 which measures the intensity of the fluorescence.

Of course, this system can be configured in various ways. For example, a light source may be used that causes the light to simultaneously impinge on the lens 331 at different discrete or continuous angles, thus illuminating several points or an entire area on the surface of the measuring chip 311. If in place of the one detector a linear detector array or an area matrix (such as a CCD array) is used, several regions of the measuring chip can be measured at the same time.

As a rule, the substances to be measured are dissolved and applied on the substrate in the form of a liquid sample. Here it is important to maintain minimal expansion of the drops on the surface. It has been found that especially in the case of deep grating valleys the droplets tend to spread due to the capillary effect that the valleys have on the droplets. In extreme cases the drops even merge. This can be counteracted by blocking the valleys with flow barriers such as continuous walls that extend in a transverse direction relative to the grating ridges. Walls of this type can be produced by applying dielectric material on the platform through a mask. Typical diameters of individual measuring fields, hereinafter referred to as spot diameters, are currently 80 μm to 200 μm. However, the distance between two walls should desirably be smaller by at least a factor of three and preferably by a factor of five to ten than the targeted spot diameter to ensure that no two droplets will share the same interstitial space.

So far, only those methods have been discussed that measure specifically binding substances on the basis of fluorescence markers. Obviously, however, the system per this invention permits direct measuring methods as well, meaning measuring methods that do not require specific markers. A detailed description of such label-free methods can be found for instance in WO 86/07149. A measurement of that type may be aimed for instance at the determination of refraction changes in a substance to be measured which would be liquid in this example and would fill the valleys in the grating. A change in the refractive index of the substance being measured will cause a change in the refractive index in the area of the valleys. Such change will directly affect the configuration of the grating and of the field intensity distribution generated thereon. The change can be measured by different methods, given the direct influence on the reflected and/or transmitted diffraction orders (zero as well as higher orders). Of course, spectral and/or angular measurements, i.e. the measurement of one or several spectral orders as a function of wavelength, are possible as well.

Label-free selective measurement is possible for instance by chemisorption or physisorption, adsorption, desorption and/or chemical bonding (hereinafter collectively referred to as substance reaction) of substances to be measured on the surface. That leads to a mensurable change in the configuration of the overall measuring-chip and especially the grating layout that codetermines the configuration of the field distribution. For example, such substance reaction can change the space or fill factor of the grating, which, however, contributes decisively to the diffraction efficiency. It is understood that selectivity of such substance reaction can also be achieved by means of an additional layer which, based on the key-lock principle, specifically binds with the substance to be measured. For example, at the beginning of the measuring process only antibodies may bind with the grating surface, primarily following the grating valleys. In the course of the measurement the corresponding antigens attach themselves, thus changing the grating configuration.

One particularly interesting feature is the possibility to directly integrate a filter on the systems per this invention. This can be accomplished by coating the grating structures in such fashion that the grating valleys are filled only slightly or not at all while the coating material is largely deposited on the grating ridges, a coating process implementable for instance by employing sputtering technology. In this case, as the thickness of the coating increases, the grating valley grows narrower. The result is a channel that is tapered toward the surface, meaning that by appropriate coating it is possible to arrive at an opening of any desired width that is equal to or smaller than the original width of the valley. Particles in the measured substance that are larger in diameter than the width of the channel cannot be diffused into the valleys, thus allowing for integrated mechanical filtering. It is possible to produce the tapered channel from an alternating layer assembly whose material and layer-thickness distribution can be optimized for the respective optical requirements.

WO 86/07149 describes a membrane that prefilters the substances to be measured, thus establishing a preselection. The systems according to this invention may also be provided with such an additional prescreening membrane. The system will be particularly suitable for the analysis of biological processes that involve so-called messenger substances. In certain biological processes, for example, a specific substance penetrating on one side of the membrane triggers a specific reaction on the other side of the membrane. In one such reaction, messenger substances may exit from the membrane and diffuse into the adjoining medium. Messenger substances of this type can occasionally cause changes in the pH value. Solutions can be prepared in such fashion that the change in the pH value changes the color of the solution. In most cases, the change in color occurs via a change in the light-absorbing properties of the solution, and that in turn has an effect on the field distribution in the grating area, which according to the examples described above is mensurable by virtue of this invention.

Different forms of implementation of the systems per this invention have been described. The layer assembly needed for these can be produced by a variety of coating processes with which those skilled in the art are familiar, such as thermal evaporation, PVD, CVD and especially PECVD or PICVD, as well as others. Interference processes are suitable for producing the grating structure, especially processes based on exposing a photosensitive layer by dual-beam interference or employing phase masks. Using conventional lithographic techniques, the grating structures created in the photosensitive layer are then transferred into the layer underneath.

One problem in that context may exist if the layer assembly underneath the grating area interferes with the exposure that generates the grating. In that case it may be better to switch to an embossing technique whereby for instance a polymer is applied on the layer assembly and by means of an embossing die a grating is then stamped into it. The subsequent lithographic process then transfers the grating into the layer underneath it. Another way to circumvent the problem is to select a system according to this invention whose grating is produced in the substrate from where the structural elements of the grating are transferred all the way to the surface. That design as well makes it possible, according to the invention, to concentrate the major part of the developing electromagnetic field in the grating structure including the grating valleys that are accessible to the substances to be measured.

The design and implementation forms of the invention as discussed above serve as examples only to which the object of the invention is not limited. One could for instance consider different illumination variations:

All of the examples discussed employed TE-polarized light, but the object of this invention is also to include impingement by TM-polarized light.

In the examples, only non-conical light impingement was mentioned. It is equally possible, however, to use conical-impingement configurations.

Design variations can be considered that use coherent, noncoherent or semicoherent light.

Design variations per this invention can be implemented with polarized or with non-polarized light. With specially selected polarization, for instance circular polarization, measurements for instance of phase shifts and especially of phase-shift changes become possible.

Suitable light sources include wide-band and/or narrow-band and/or monochromatic light sources. Among others, it is possible to use continuous or pulsed lasers and especially semiconductor lasers, light-emitting diodes (LEDs) and incandescent lamps.

The impinging light may come from different directions:
from the substrate side
from the superstrate side by way of a possibly structured waveguide additionally integrated in the system per this invention or from a combination of one or the other or several or all of the above.

So far, the description only refers to grating structures with unidimensional rectangular grating profiles. Here again, it is possible, and an object of this invention, to use design variations of the invention employing more general types of grating structures, such as:

unidimensional gratings with other than rectangular profiles and/or space/fill factors other than 0.5;

unidimensional gratings with two or more superposed grating periodicities whose grating vectors are mutually parallel;

two-dimensional gratings, i.e. periodic structures with at least two nonparallel grating vectors (crossed gratings), with those two-dimensional gratings being of particular interest in terms of their polarization effect that exhibit grating vectors extending perpendicular to each other and/or being quantitatively identical;

periodic structures which themselves are composed of layer assemblies.

Already described above as a partial aspect of this invention is the possibility to concentrate the high field distribution in an area of the grating in which the refractive indices of the materials involved are equal to or smaller than the refractive index of the substrate.

As another partial aspect of the invention, the grating valleys make it possible for regions of maximum field intensity to be accessible to the substances being measured. This inventive aspect is also achievable with a structured grating segment in which one or several of the materials involved have a refractive index that is greater than that of the substrate.

The above examples only describe systems in which the inventive effects are obtained with the exclusive use of dielectric materials. However, it is also possible to produce design variations per this invention that comprise metallic materials and especially structured metallic materials. Moreover, design versions can be produced that combine the inventive effects (high-intensity field in the grating valleys that are accessible to the substances being measured) with prior-art effects and most particularly with surface plasmons.

This description has focused on the use of a system per this invention in the realm of sensory analysis. Indeed, this inventive system can be applied wherever substances are to be exposed to light in close proximity (i.e. in the range of up to about 10 wavelengths from the surface). The fact that, for instance in the system per FIG. 5, nearly 4 field-intensity maxima are produced within one grating period, also makes it possible to locally expose a photosensitive layer in such fashion that a nearly four times smaller grating period can be implemented.

LIST OF REFERENCE NUMBERS

97 System
101 Substrate
103 Periodic grating
107 Dielectric layer
109 Biological coupling elements
113 Superstrate
11 System
13 Substrate
17 Layer assembly
19 Grating structure
23 Grating ridges
29 Grating valleys
31 Biological coupling elements on the bottom of the valleys
31' Biological coupling elements on the lateral walls
31" Biological coupling elements on the grating ridges
37 Superstrate
211 System
223 Substrate
227 Layer assembly
229 Grating area
233 Biological binder molecules on the bottom of the valleys
233' Biological binder molecules on the lateral walls
233" Biological binder molecules on the grating ridges
239 Superstrate
307 Measuring system
311 Measuring chip
313 Light source
317 Selective mirror
331 Lens
337 Detector
LA Excitation light
LF Fluorescent light
5 Line of identical square amplitudes with a value of 5
10 Line of identical square amplitudes with a value of 10
15 Line of identical square amplitudes with a value of 15
20 Line of identical square amplitudes with a value of 20
50 Line of identical square amplitudes with a value of 50
100 Line of identical square amplitudes with a value of 100
150 Line of identical square amplitudes with a value of 150
200 Line of identical square amplitudes with a value of 200
250 Line of identical square amplitudes with a value of 250
500 Line of identical square amplitudes with a value of 500
750 Line of identical square amplitudes with a value of 750
1000 Line of identical square amplitudes with a value of 1000

What is claimed is:

1. Platform for generating an electromagnetic field distribution, comprising
    a substrate
    a structured layer provided on the substrate
    coupling means for coupling impinging electromagnetic radiation into said structured layer so as to generate an electromagnetic field distribution within the structured layer
    a multilayer assembly between the substrate and the structured layer, said multilayer assembly forming means for at least substantially decoupling the electromagnetic field distribution in the structured layer from the substrate with regard to spectral orders other than zero order.

2. Platform as in claim 1, wherein the structured layer has a first refractive index and the substrate has a second refractive index, and further wherein the first refractive index is less than 1% greater than the second refractive index.

3. Platform as in claim 1, wherein a profile of the structured layer encompasses periodically spaced conformations that constitute a part of the coupling means.

4. Platform as in claim 1, wherein the multilayer assembly comprises metallic layers consisting of Al and/or Ag.

5. Platform as in claim 1, wherein the multilayer assembly comprises dielectric layers and no metallic layers.

6. The platform of claim 1, said multilayer assembly forming means for completely decoupling the electromagnetic field distribution in the structured layer from the substrate with regard to spectral orders other than zero order.

7. The platform of claim 1, wherein the structured layer has a first refractive index and the substrate has a second refractive index, and further wherein the first refractive index is lower than the second refractive index.

8. A measuring system, comprising:
   a light source;
   a detector; and
   a measuring chip including the platform of claim 1, wherein the light source produces a light beam for impingement on the measuring chip.

9. The platform of claim 5, wherein the multilayer assembly is constructed in an alternating layer fashion with alternating high- and low-refraction layers.

10. Method for generating an enhanced and not exclusively evanescent electromagnetic field distribution, comprising the following steps of:
   selecting a substrate
   selecting a first material for and a structural profile of a structured layer
   selecting a second material for a multilayer assembly
   defining parameters of an electromagnetic radiation to be employed for an exposure
   simulating and optimizing the electromagnetic field distribution within a platform comprising the substrate, the multilayer assembly and the structured layer upon impingement by electromagnetic radiation of the defined parameters, with the multilayer assembly positioned between the substrate and the structured layer and an objective of the step of optimizing being a field distribution that is at its maximum within the structured layer;
   constructing the platform in a manner that at least approximates a result of the step of optimizing, wherein said multilayer assembly forms means for at least substantially decoupling the electromagnetic field distribution in the structured layer from the substrate with regard to spectral orders other than zero order; and
   impinging the electromagnetic radiation on the platform along the defined parameters.

11. Method as in claim 10, wherein a second objective of the step of optimizing is a field distribution that exhibits at least one maximum in regions of the structured layer that are devoid of the first material.

12. A platform for generating an electromagnetic field distribution, comprising:
   a substrate;
   a structured layer provided on the substrate, said structured layer forming diffraction structures for coupling impinging electromagnetic radiation into said structured layer so as to generate an electromagnetic field distribution within the structured layer;
   a multilayer assembly located between the substrate and the structured layer, said multilayer assembly forming means for substantially decoupling the electromagnetic field distribution in the structured layer from the substrate with regard to spectral orders other than zero order, wherein a diffractive efficiency of said diffraction structures is chosen such that the diffraction structures and the multilayer assembly together cause the electromagnetic field distribution to have a maximum intensity within the structured layer.

13. Sensor with a platform as in claims 1, 2, 3, 4, 5, 7, 9 or 12 wherein the sensor is adapted to measure specific substances in a biological and/or chemical and/or biochemical sample.

* * * * *